United States Patent [19]

Shimada et al.

[11] Patent Number: 5,510,437
[45] Date of Patent: Apr. 23, 1996

[54] ORGANOPLATINUM POLYMER AND METHOD FOR PRODUCING THE SAME

[75] Inventors: Shigeru Shimada; Masato Tanaka, both of Tsukuba, Japan

[73] Assignee: Director-General of Agency of Industrial Science and Technology, Tokyo, Japan

[21] Appl. No.: 398,170

[22] Filed: Mar. 2, 1995

[30] Foreign Application Priority Data

Mar. 11, 1994 [JP] Japan ..................................... 6-068018

[51] Int. Cl.$^6$ .......................... C08F 238/00; C08F 230/04
[52] U.S. Cl. ................. 526/241; 528/9; 556/136
[58] Field of Search ................................ 526/241; 528/9; 556/136

[56] References Cited

U.S. PATENT DOCUMENTS

| | | | |
|---|---|---|---|
| 4,603,215 | 7/1986 | Chandra et al. | 556/136 |
| 5,072,069 | 12/1991 | Wenski et al. | 585/277 |

*Primary Examiner*—Mark Nagumo
*Attorney, Agent, or Firm*—Birch, Stewart, Kolasch & Birch

[57] ABSTRACT

There is disclosed a method for producing organoplatinum polymers by reacting 5,6,11,12-tetradehydrodibenzo[a,e]cyclooctenes with platinum complexes. The organoplatinum polymer thus obtained has $\pi$-coordinated acetylene in the main chain, and is expected to be used as electronic materials, nonlinear optical materials, and polymer platinum complex catalysts, that can be used in air.

10 Claims, No Drawings

ORGANOPLATINUM POLYMER AND METHOD FOR PRODUCING THE SAME

FIELD OF THE INVENTION

The present invention relates to organoplatinum polymers that can be used as electronic materials such as electroconductive materials, nonlinear optical materials, platinum complex polymer catalysts, and the like, and to a method for efficiently producing them.

BACKGROUND OF THE INVENTION

Organometallic polymers have, in addition to the properties possessed by conventional carbon-type polymers, the properties possessed by organometallic complexes, and they are expected to have new properties that will arise from combinations of a carbon-type polymer and an organometallic complex. Particularly, organometallic polymers are noticeable as electronic materials and nonlinear optical materials. Hitherto, various organometallic polymers have been known (e.g., Polymers, 42, 572 (1993); and J. Am. Chem. Soc., 115, 7035 (1993)). However, organoplatinum polymer containing π-coordinated acetylene in the main chain, and a method for producing the same, are not yet known.

SUMMARY OF THE INVENTION

An object of the present invention is to provide a method for efficiently producing organoplatinum polymers.

Another object of the present invention is to provide novel organoplatinum polymers obtained by the above method.

Other and further objects, features, and advantages of the invention will appear more fully from the following description.

DETAILED DESCRIPTION OF THE INVENTION

The present inventors, having keenly studied to attain the above objects, have found that specific 5,6,11,12-tetradehydrodibenzo[a,e]cyclooctenes and specific platinum complexes interact quickly, under mild conditions, to give organoplatinum polymers. Based on the finding, the present invention has been completed.

That is, the present invention provides:

(1) a method for producing organoplatinum polymers represented by the following formula (III):

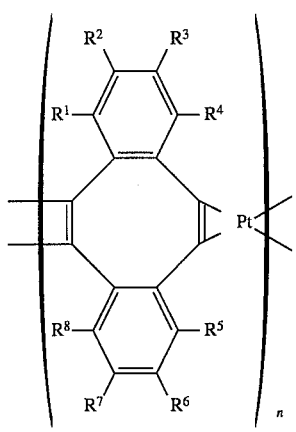

formula (III)

wherein $R^1$, $R^2$, $R^3$, $R^4$, $R^5$, $R^6$, $R^7$, and $R^8$ each represent a monovalent group, and n is a positive integer, comprising reacting (a) 5,6,11,12-tetradehydrodibenzo-[a,e]cyclooctenes represented by the following formula (I):

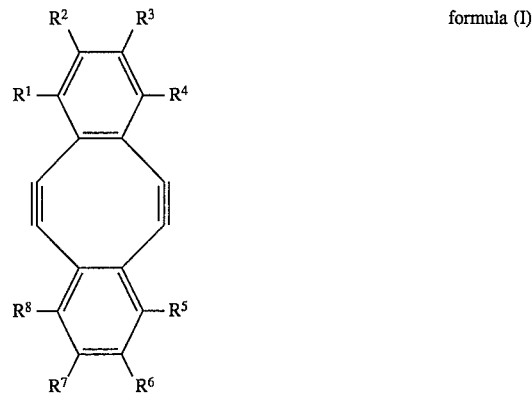

formula (I)

wherein $R^1$, $R^2$, $R^3$, $R^4$, $R^5$, $R^6$, $R^7$, and $R^8$ have the same meaning as defined above, with (b) platinum complexes represented by the following formula (II):

formula (II)

$Pt_xL_y$ wherein L represents a ligand, and x and y are each a positive integer. In the above formula (III), n is generally 2 or more, preferably 5 or more, and more preferably 10 to 2,000.

The present invention also provides:

(2) compounds represented by the above formula (III).

In the above-mentioned method of the present invention, it is considered that the reaction proceeds in accordance with the following formula (IV):

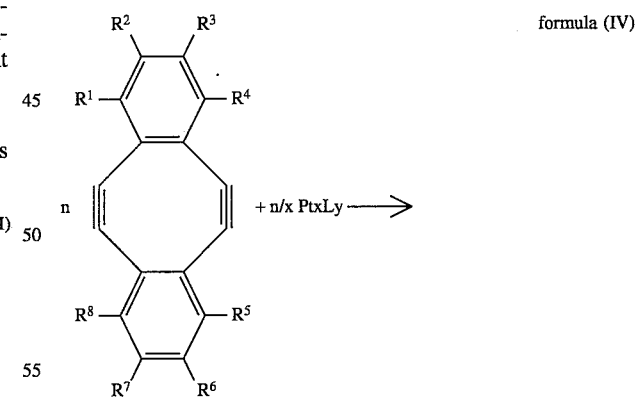

formula (IV)

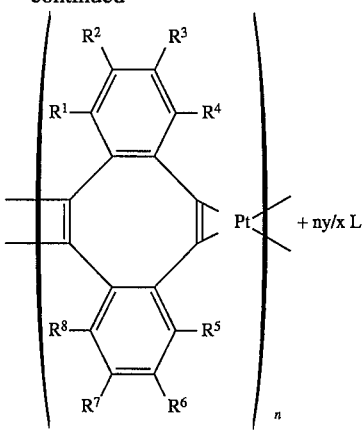

wherein $R^1$, $R^2$, $R^3$, $R^4$, $R^5$, $R^6$, $R^7$, and $R^8$ each represent a monovalent group, and x, y, and n are each a positive integer.

The 5,6,11,12-tetradehydrodibenzo[a,e]-cyclooctenes used in the present invention are represented by formula (I):

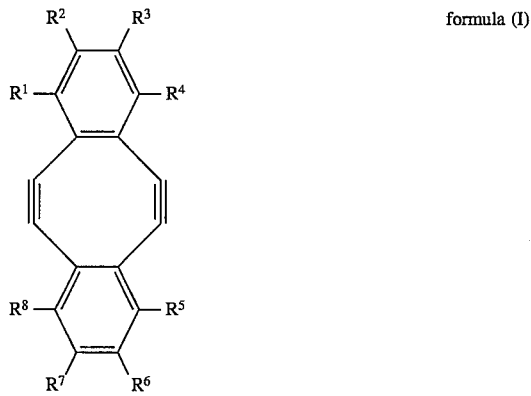

formula (I)

wherein $R^1$ to $R^8$ each represent a monovalent group; for example, a hydrogen atom, a halogen atom, a cyano group, an alkyl group, an aryl group, an aralkyl group, an alkoxy group, or an alkoxycarbonyl group, each having 1 to 20 carbon atoms. Examples of 5,6,11,12-tetradehydrodibenzo[a,e]cyclooctenes represented by formula (I) having such substituents are 5,6,11,12-tetradehydrodibenzo[a,e]cyclooctene, 2-pentyl-5,6,11,12-tetradehydrodibenzo[a,e]cyclooctene, 2-octyl-5,6,11,12-tetradehydrodibenzo[a,e]cyclooctene, 2-phenyl-5,6,11,12-tetradehydrodibenzo[a,e]cyclooctene, 2-methoxy-5,6,11,12-tetradehydrodibenzo[a,e]cyclooctene, 2-chloro-5,6,11,12-tetradehydrodibenzo[a,e]cyclooctene, methyl 5,6,11,12-tetradehydrodibenzo[a,e]cyclooctene-2-carboxylate, 5,6,11,12-tetradehydrodibenzo[a,e]cyclooctene-2-carbonitrile, 2,3-dipentyl-5,6,11,12-tetradehydrodibenzo[a,e]cyclooctene, 2,3-diheptyl-5,6,11,12-tetradehydrodibenzo[a,e]cyclooctene, 2,3,8,9-tetrapentyl-5,6,11,12-tetradehydrodibenzo[a,e]cyclooctene, and 2,3,8,9-tetraheptyl-5,6,11,12-tetradehydrodibenzo[a,e]cyclooctene.

The 5,6,11,12-tetradehydrodibenzo[a,e]cyclooctenes used in the present invention can be synthesized by methods described in the literature (e.g., Tetrahedron, 37, Supplement No. 1, 99 (1981)).

The platinum complexes used in the present invention are represented by formula (II):
formula (II)

$$Pt_xL_y$$

The value of x/y is generally from 1/6 to 1, and preferably from 1/4 to 1, and x is generally from 1 to 10, preferably from 1 to 5, and more preferably 1 or 2. In the formula (II), L is a ligand, and examples of preferable ligands are olefins, acetylenes, conjugated ketones, phosphines, phosphonites, phosphinites, phosphites, amines, and carbon monoxide. Specific examples include an olefin, such as ethylene, propene, cyclooctene, maleic anhydride, 1,5-hexadiene, 1,5-cyclooctadiene, 1,3-cyclopentadiene, 2,5-norbornadiene, and 1,3,5,7-cyclooctatetraene; an acetylene, such as diphenylacetylene and dimethyl acetylenedicarboxylate; a conjugated ketone, such as dibenzylidene acetone; a phosphine, such as trimethylphosphine, tributylphosphine, triethylphosphine, tricyclohexylphosphine, triphenylphosphine, tri(p-tolyl)phosphine, tri(p-anisyl)phosphine, diphenylmethylphosphine, and phenyldimethylphosphine; a cyclic phosphine, such as P-methylphospholene, P-methylphosphole, and 9-methyl-9-phosphabicyclo[4.2.1]nonane; a bisphosphine, such as 1,2-bis(dimethylphosphino)ethane, 1,3-bis(dimethylphosphino)propane, 1,4-bis(dimethylphosphino)butane, 1,2-bis(diphenylphosphino(ethane, 1,3-bis(diphenylphosphino)propane, 1,4-bis(diphenylphosphino)butane, 1,1'-bis(dimethylphosphino)ferrocene, 1,1'-bis(diphenylphosphino)ferrocene, α,α'-bis(dimethylphosphino)-o-xylene, and 1,2-bis(dimethylphosphino)benzene; a phosphonite, such as dimethyl methylphosphonite and dimethyl phenylphosphonite; a phosphinite, such as methyl dimethylphosphinite and phenyl diphenylphosphinite; a phosphite, such as triethylphosphite, triphenylphosphite, and 1-phospha-2,6,7-trioxa-4-ethylbicyclo[2.2.2]octane; an amine, such as ethylenediamine and 2,2'-bipyridyl; and carbon monoxide.

Thus, specific examples of the platinum complexes used in the present invention include bis(η-1,5-cyclooctadiene)platinum, tris(ethylene)platinum, bis(diphenylacetylene)platinum, (η-ethylene)bis(triphenylphosphine)platinum, tetrakis(triethylphosphine)platinum, tetrakis(triphenylphosphine)platinum, tetrakis(diphenylmethylphosphine)platinum, and tris(dibenzylideneacetone)diplatinum, but the present invention is not limited to them.

In the production method of the present invention, the ratio of 5,6,11,12-tetradehydrodibenzo[a,e]cyclooctenes to the platinum complexes is such that, generally, the molar ratio of the 5,6,11,12-tetradehydrodibenzo[a,e]cyclooctene to the platinum complex is in the range of from 1:20 to 20:1, and preferably from 1:3 to 3:1.

To carry out the reaction of the present invention, a solvent is not necessarily required, but preferably a solvent is used to permit the reaction to proceed smoothly. In order to select a solvent to be used, for example, the reactivity and the solubility of the 5,6,11,12-tetradehydrodibenzo[a,e]cyclooctenes and the platinum complexes to be reacted are taken into consideration. Preferably a solvent that is generally used, such as a hydrocarbon solvent, a halogenated solvent, or an ether solvent, is selected.

Although the reaction of the present invention proceeds at 0° C. or below, the reaction can be carried out by heating the reactants to a temperature of 200° C., in order to attain a preferable reaction rate. Generally, a preferable temperature range is from 0° to 100° C., with the temperature varying depending on the structure of the raw materials.

There is no restriction on the reaction time or pressure in the production processes of the present invention. Preferable time period for the reaction is 1 minutes to 48 hours. The reaction can be conducted under ordinary pressure.

Preferably, the reaction in the production processes of the present invention is carried out under an inert gas atmosphere, such as nitrogen, argon, or helium gas.

The end group of the polymer represented by formula (III) may be a C—C triple bond or a platinum atom that is coordinated with ligands. In the latter case, ligands are those represented by L, which is derived from platinum complex of the formula $Pt_xL_y$, used as a raw material of the polymer. The number of the ligands is generally y/2x, or it may be an integer around y/2x.

Recovery of the product after the reaction is easily carried out by a usually used means, such as filtration or reprecipitation.

The π-coordinated acetylenes (5,6,11,12-tetradehydrodibenzo[a,e]cyclooctenes) used in the present invention are cyclic diyne compounds having a planar conjugated structure, in which two acetylenes are linked with two benzene rings. The π-coordinated acetylene has a conjugated system through the whole molecule. Thus, in the organoplatinum polymer of the present invention, which polymer has π-coordinated acetylenes alternatively π-coordinated with platinum atoms to be in a line, π-electrons may delocalize in the whole molecule through platinum atoms, and electroconductivity and nonlinear optical characteristics may be expressed.

The organoplatinum polymers of the present invention may be used as catalyst in the same manner as described, for example, in Caseri, W. and Pregosin, P. S., Organometallics, 7, 1373–1380 (1988); Marciniec, B., Gulinski, J., Urbaniak, W., Nowicka, J., and Nirecki, J., Applied Organometallic Chemistry, 4, 27–34 (1990); M. Tanaka, Y. Uchimaru, and H.-J. Lautenschlager, Organometallics, 10, 16 (1991); and Y. Uchimaru, A.M.M. El Sayed, and M. Tanaka, Organometallics, 12, 2065 (1993), which disclose that organoplatinum complexes having η-coordinated olefins are used as catalyst.

According to the present invention, organoplatinum polymers can be easily obtained from 5,6,11,12-tetradehydrodibenzo[a,e]cyclooctenes and platinum complexes. Although known organoplatinum compounds were generally unstable in air and against heat, the organoplatinum polymers of the present invention, as organometallic compounds, are quite stable; for example, the decomposition temperature, as shown in Example 1, is 200° C. or over in air. Therefore, the compounds of the present invention has utility as electronic materials, nonlinear optical materials, and polymer platinum complex catalysts, that can be used in the air, and the present invention's industrial significance is great.

The present invention will now be described with reference to the following Example, but the present invention is not restricted to the Example.

EXAMPLE 1

Eight ml dichloromethane was added to 64.7 mg (0.16 mmol) of bis(η-1,5-cyclooctadiene)platinum under a nitrogen atmosphere, to dissolve it, and then immediately 31.5 mg (0.16 mmol) of 5,6,11,12-tetradehydrodibenzo[a,e]cyclooctene was added. After stirring for 3 hours at room temperature, the produced precipitate was filtered through a glass filter and was washed with dichloromethane, to obtain a brownish orange powder of a compound represented by the below-given formula. The yielded amount was 61 mg and the yield was 98%. The compound was insoluble in usual organic solvents.

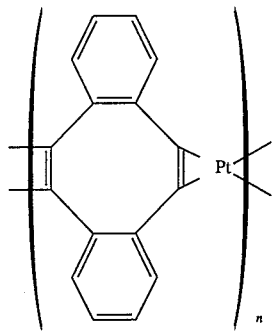

(This polymer is an organoplatinum polymer corresponding to formula (III), wherein $R^1$ to $R^8$ each represent a hydrogen atom.)

The compound is a novel compound that has not yet appeared in the literature, and the values of its physical properties and its spectrum data were as follows.

Melting point: 200° C. or over (decomposed)

IR (KBr): 3058, 1864, 1584, 1468, 1437, 1257, 1156, 1085, 1035, 946, 857, 781, 754, 679, 634, 601, 532, 478 $cm^{-1}$

Elementary analysis: $(C_{16}H_8Pt)_n$ (Calculated): C 48.61%; H 2.04%

(found): C 48.48%; H 2.13%

Having described our invention as related to the present embodiments, it is our intention that the invention not be limited by any of the details of the description, unless otherwise specified, but rather be construed broadly within its spirit and scope as set out in the accompanying claims.

What we claim is:

1. A method for producing organoplatinum polymers represented by the following formula (III):

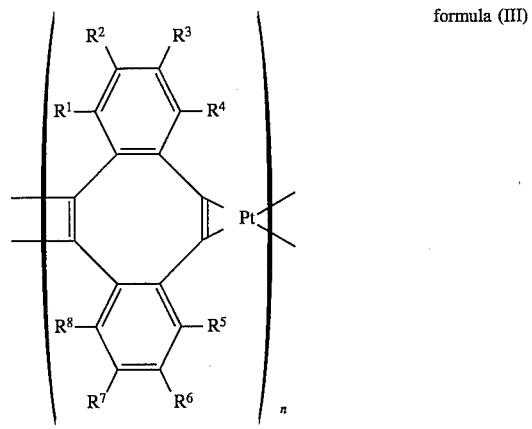

formula (III)

wherein, $R^1$, $R^2$, $R^3$, $R^4$, $R^5$, $R^6$, $R^7$, and $R^8$ each represent a monovalent group, and n is 2 or more, comprising reacting (a) 5,6,11,12-tetradehydrodibenzo[a,e] cyclooctenes represented by the following formula (I):

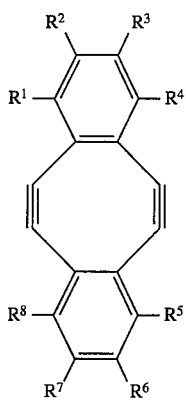

formula (I)

wherein $R^1$, $R^2$, $R^3$, $R^4$, $R^5$, $R^6$, $R^7$, and $R^8$ have the same meaning as defined above,
with (b) platinum complexes represented by the following formula (II):

formula (II)

$$Pt_xL_y$$

wherein L represents a ligand, and x and y are each a positive integer.

2. The method for producing organoplatinum polymers as claimed in claim 1, wherein $R^1$, $R^2$, $R^3$, $R^4$, $R^5$, $R^6$, $R^7$, and $R^8$, which are the same or different, are each a hydrogen atom, a halogen atom, a cyano group, an alkyl group having 1 to 20 carbon atoms, an aryl group having 6 to 20 carbon atoms, an aralkyl group having 7 to 20 carbon atoms, an alkoxy group having 1 to 20 carbon atoms, or an alkoxycarbonyl group having 2 to 20 carbon atoms.

3. The method for producing organoplatinum polymers as claimed in claim 1, wherein L is an olefin, an acetylene, a conjugated ketone, a phosphine, a phosphonite, a phosphinite, a phosphite, or an amine.

4. The method for producing organoplatinum polymers as claimed in claim 1, wherein the value of x/y is from ⅙ to 1, and x is from 1 to 10.

5. The method for producing organoplatinum polymers as claimed in claim 4, wherein x is from 1 to 5.

6. The method for producing organoplatinum polymers as claimed in claim 1, wherein the molar ratio of the 5,6,11,12-tetradehydrodibenzo[a,e]cyclooctene to the platinum complex is in the range of from 1:20 to 20:1.

7. The method for producing organoplatinum polymers as claimed in claim 1, wherein the reaction is carried out in a hydrocarbon solvent, a halogenated solvent, or an ether solvent.

8. The method for producing organoplatinum polymers as claimed in claim 1, wherein the reaction is carried out at a temperature in the temperature range of from 0° C. to 100° C.

9. An organoplatinum polymer represented by the following formula (III):

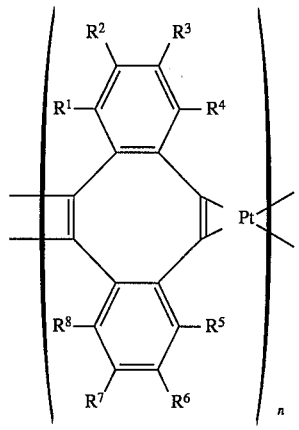

formula (III)

wherein $R^1$, $R^2$, $R^3$, $R^4$, $R^5$, $R^6$, $R^7$, and $R^8$ each represent a monovalent group, and n is 2 or more.

10. The organoplatinum polymers as claimed in claim 9, wherein $R^1$, $R^2$, $R^3$, $R^4$, $R^5$, $R^6$, $R^7$, and $R^8$, which are the same or different, are each a hydrogen atom, a halogen atom, a cyano group, an alkyl group having 1 to 2 carbon atoms, an aryl group having 6 to 20 carbon atoms, an aralkyl group having 7 to 20 carbon atoms, an alkoxy group having 1 to 20 carbon atoms, or an alkoxycarbonyl group having 2 to 20 carbon atoms.

* * * * *